United States Patent
Platt et al.

(10) Patent No.: US 10,206,089 B2
(45) Date of Patent: *Feb. 12, 2019

(54) METHOD AND SYSTEM FOR ESTABLISHING RF AWARE AND SST AWARE COMMUNICATIONS NETWORKS WHERE NETWORK AWARE DEVICES MAY DETECT, DISCOVER, AUTHENTICATE AND COMMUNICATE DIRECTLY WITH EACH OTHER, BASED ON SUCH ATTRIBUTES AS INTERESTS, PROXIMITY, OR LOCATION WITHIN OR OUTSIDE OF A SPECIFIED ZONE

(71) Applicants: Timo Platt, Portsmouth, NH (US);
Stephan Krueger, Salem, NH (US);
Barbara Roselle, Andover, MA (US)

(72) Inventors: Timo Platt, Portsmouth, NH (US);
Stephan Krueger, Salem, NH (US);
Barbara Roselle, Andover, MA (US)

(73) Assignee: Pokos Communications Corp, Bozeman, MT (US)

( * ) Notice: Subject to any disclaimer, the term of this patent is extended or adjusted under 35 U.S.C. 154(b) by 124 days.

This patent is subject to a terminal disclaimer.

(21) Appl. No.: 15/084,376

(22) Filed: Mar. 29, 2016

(65) Prior Publication Data
US 2016/0242023 A1 Aug. 18, 2016

Related U.S. Application Data

(63) Continuation of application No. 13/870,456, filed on Apr. 25, 2013, now Pat. No. 9,374,397.

(51) Int. Cl.
*H04W 8/00* (2009.01)
*H04L 29/06* (2006.01)
(Continued)

(52) U.S. Cl.
CPC ............ *H04W 8/005* (2013.01); *G06Q 30/02* (2013.01); *G06Q 30/0256* (2013.01);
(Continued)

(58) Field of Classification Search
CPC ......... H04W 8/005; H04W 4/02; H04W 4/06; H04W 12/06; H04W 76/023; G06Q 30/02;
(Continued)

(56) References Cited

U.S. PATENT DOCUMENTS 8,284,748 B2 10/2012 Borghei
8,384,684 B2 2/2013 Westerman
(Continued)

OTHER PUBLICATIONS

Andreas Heinemann, "Collaboration in Opportunistic Networks", (VDM Verlag 2007) (dissertation, Darmstadt University of Technology).
(Continued)

*Primary Examiner* — Jung H Park

(57) ABSTRACT

A communications network is provided where devices are assigned either a static or random unique device identifier; where devices may be configured to be in public or private mode; and, where devices are in public mode, they may detect, discover, authenticate and communicate directly with each other, based on such attributes as interests, proximity, or location within or outside a specified zone.

4 Claims, 1 Drawing Sheet

(51) Int. Cl.
G06Q 30/02 (2012.01)
H04W 4/02 (2018.01)
H04L 29/08 (2006.01)
H04W 4/06 (2009.01)
H04W 12/06 (2009.01)
H04W 76/14 (2018.01)

(52) U.S. Cl.
CPC .......... H04L 65/403 (2013.01); H04L 67/125 (2013.01); H04L 67/16 (2013.01); H04L 67/18 (2013.01); H04L 67/42 (2013.01); H04W 4/02 (2013.01); H04W 4/06 (2013.01); H04W 12/06 (2013.01); H04W 76/14 (2018.02)

(58) Field of Classification Search
CPC . G06Q 30/0256; H04L 65/403; H04L 67/125; H04L 67/16; H04L 67/18; H04L 67/42
See application file for complete search history.

(56) References Cited

U.S. PATENT DOCUMENTS

| | | | |
|---|---|---|---|
| 8,385,039 B2 | 2/2013 | Rothkopf | |
| 8,401,009 B1 | 3/2013 | Dorsey et al. | |
| 8,417,575 B2 | 4/2013 | Nakijima et al. | |
| 8,417,779 B2 | 4/2013 | Weber | |
| 2007/0171910 A1* | 7/2007 | Kumar | H04L 63/0428 370/392 |
| 2013/0099892 A1 | 4/2013 | Tucker et al. | |
| 2013/0103200 A1 | 4/2013 | Tucker et al. | |
| 2013/0137373 A1* | 5/2013 | Choi | H04B 5/0031 455/41.1 |
| 2014/0068023 A1* | 3/2014 | Arickan | H04L 61/2015 709/220 |

OTHER PUBLICATIONS

Wi-Fi Alliance, "Wi-Fi Aware™: Discover the World Nearby, Enabling Personalized Social, Local and Mobile Experiences" (Jul. 2015 Austin, Texas USA).

Wi-Fi Alliance, "Neighbor Awareness Networking, Technical Specification, Version 1.0" copyright 2015 (Austin, Texas USA).

* cited by examiner

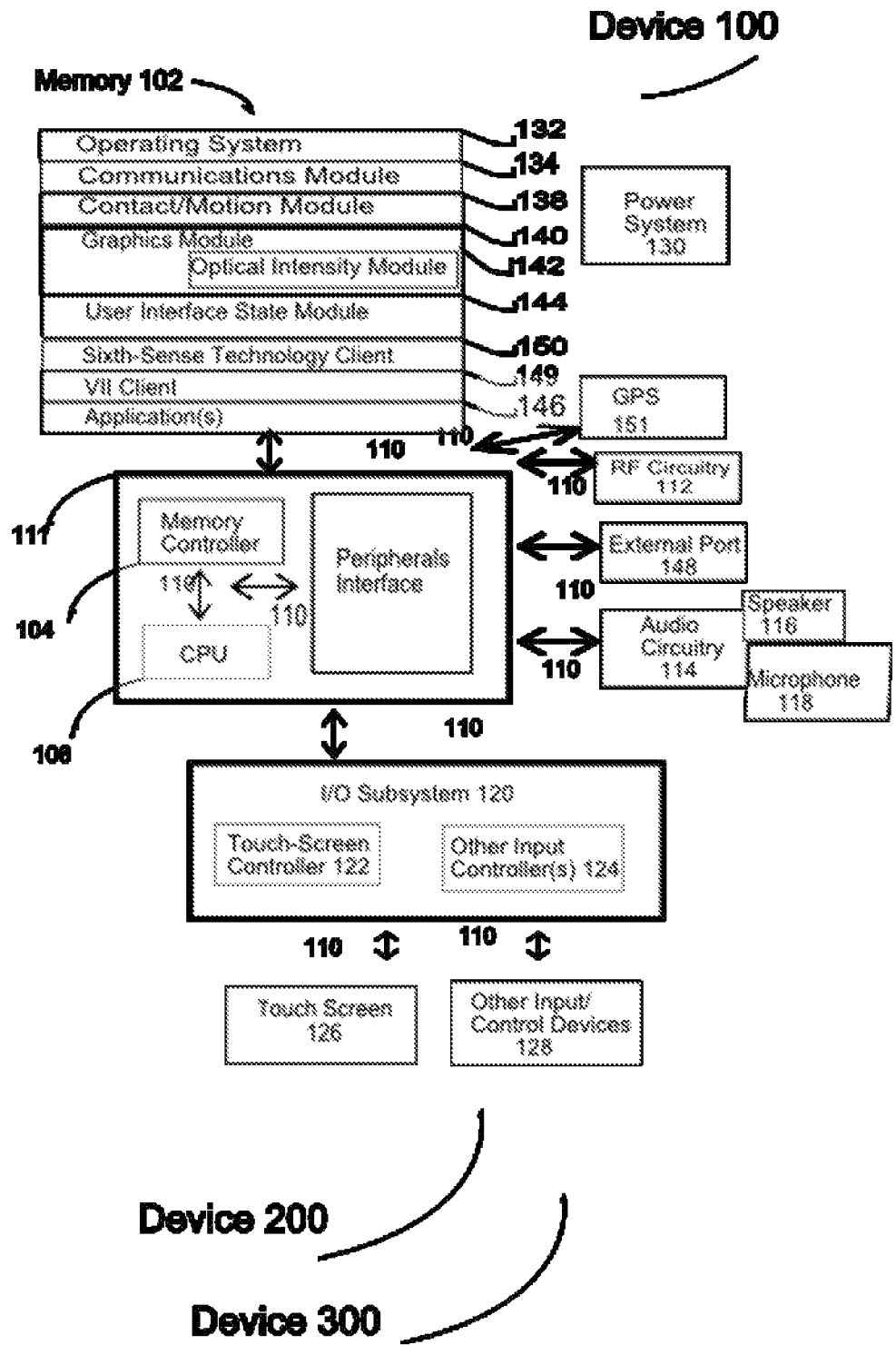

METHOD AND SYSTEM FOR ESTABLISHING RF AWARE AND SST AWARE COMMUNICATIONS NETWORKS WHERE NETWORK AWARE DEVICES MAY DETECT, DISCOVER, AUTHENTICATE AND COMMUNICATE DIRECTLY WITH EACH OTHER, BASED ON SUCH ATTRIBUTES AS INTERESTS, PROXIMITY, OR LOCATION WITHIN OR OUTSIDE OF A SPECIFIED ZONE

CROSS-REFERENCE TO RELATED APPLICATIONS

The present application is a continuation of U.S. application Ser. No. 13/870,456 filed on Apr. 25, 2013 (the "Patent Application") entitled "Method and system for searching, sensing, discovering, screening, enabling awareness, alerting, sharing, sending, receiving, buying, selling, and otherwise transmitting stories, content, interests, data, goods and services among known and unknown devices in a communication network", in respect of which application U.S. Pat. No. 9,374,397 issued on Jun. 16, 2016 (the "Parent Patent"), which claims the benefit of U.S. Provisional Patent Application Ser. No. 61/648,212, entitled "1. Communication Methods between, among and to Unknown Devices; 2. Searching, Sending and Receiving Voice, Video and Data between, among and to Unknown Devices; 3. Creating Sixth-Sense Technologies for Sharing and Learning Stories and Interests; and 4. Discovery engine to identify others with whom to communicate" and filed on May 17, 2012. The Parent Application and Parent Patent identified above are incorporated here by reference in their entirety to provide continuity of disclosure.

BACKGROUND OF THE INVENTION

Field of the Invention

This disclosure relates generally to a method and system for searching, sensing, discovering, screening, enabling awareness, alerting, sharing, sending, receiving, buying, selling, and otherwise transmitting stories, content, interests, data, goods and services among known and unknown devices in a communication network.

Description of Related Art

General background information regarding the related art is set forth in the Parent Application and in the applicant's Information Disclosure Statement filed with this Continuation Patent Application, which background is incorporated herein by reference.

It may be argued that the current inventions are anticipated in part by Heinemann (Andreas Heinemann, *Collaboration in Opportunistic Networks* (VDM Verlag 2007) (dissertation, Darmstadt University of Technology)) ("Heinemann"), because Heinemann may disclose methods for searching, sensing, and discovering attributes, etc. among known and unknown devices.

A careful review of the Heinemann dissertation, however, reveals that the current inventions were not, and are not, anticipated by that prior publication.

Heinemann described the use of filters and profiles as a means of data dissemination in a collaborative opportunistic network (a "CON") (pp. v, 4, 5, 13-14, 18, 43-44); and also envisioned use of changing network identifiers in a collaborative network, by using public key cryptography and linking public keys to, e.g., email addresses, as a method to authenticate information items or identity and preserve anonymity in an ad hoc mobile network (pp. vi, 14, 48, 49-52, 77-78, 81, 87, 94).

The art taught by and foreseeable from Heinemann's CON has several critical limitations, which are conceded by Heinemann. First, his CONs are limited to the dissemination of broadcast-type information to others users in close proximity to each other; they do not support any message routing functionality (p. 78). Second, his ad hoc networks do not authenticate the user/device to deliver either user- or device-specific messages or other content. Third, his CONs do not enable communication with devices/users outside or beyond such closely proximate zone. (pp. 11, 15, 28, 49-52, 78, 81, 94).

The Applicant's inventions in the Parent Application, including its Claims in this Continuation Application for RF Aware and SST Aware Networks, overcome these limitations:

first by solving the problem of how to authenticate devices at both ends (i.e., sending and receiving) of a communication by using variable identification information, or VII—defined to include one or more of the searched-for attributes, varying device identifying information, or other datum or data associated with or pertinent to the device (including its software or firmware) or its user, without the use of or reliance on, e.g., public or private cryptography keys, other known contact information, or enrollment in a social network;

second, by using VII, to route messages to specific devices, thus overcoming Heinemann's limitation of only being able to send the same broadcast-type information to all devices/users;

third, by using VII, to be able to be able to authenticate and communicate with devices or users who are not in close proximity to each other;

fourth, by using VII, to maintain communications with devices or users who move outside of the same proximate location or zone; and fifth, by using VII, to re-authenticate and initiate targeted communications with specific devices or users who move outside of the same proximate location or zone; in each case without the use of or reliance on, e.g., public or private cryptography keys, other known contact information, or enrollment in a social network.

Furthermore, the current inventions combine variable identification information with search, detect and functional operations (jointly, "Sixth-Sense Technology", or simply "SST") to enable users to conduct personal and commercial activities in new ways, while giving users control over their privacy and anonymity. These inventions enables for the first time the sharing of stories and content, and the marketing, sale, purchase, and license of goods and services between or among intended but unknown devices or their users.

Applicant's inventions are not taught by or foreseeable from Heinemann and other prior art because they disclose and teach the nonobvious features that:

(a) The SST inventions use variable identification information from each of the first device and the recipient devices to authenticate and maintain directed communication by and among the first device with the recipient devices (b) The SST inventions describe a new method of communication that does not use and is not dependent upon the use of public or private cryptography keys (c) The SST Inventions describe a new method of communication that enables authentication of devices to deliver user- or device-specific messages or other content (d) The SST Inventions describe a new method of communication that enables communication with devices/users outside or beyond limited physical areas or zones (e) By combining these authentication and communications capabilities with search and detect functionalities, filters, and user attributes, the Applicant's inventions create new functional operations that enable users to conduct personal and commercial activities in new ways, while giving users control over their privacy and anonymity. The SST inventions enable for the first time the sharing of directed stories and content, and the marketing, sale, purchase, and license of goods and services between or among intended but unknown devices or their users.

None of these features is taught or suggested by Heinemann or the prior art.

Applicant is the first to recognize the advantage of combining variable identification information for authentication and communication purposes with search and detect functionalities, filters and user attributes, so that a new result—not anticipated by Heinemann or the prior art—has been achieved; that is, devices and users can communicate and share with those around them—both nearby and around the globe—to enhance their individual and social experiences, to connect them with their past and with each other, to improve their understanding and enjoyment of life, and to conduct and engage in commerce in new ways.

BRIEF SUMMARY OF THE INVENTION

RF Aware and SST Aware Networks

The Claims set forth in this Continuation Application do not contain new matter relative to the Parent Application; the Claims herein are conceived and based entirely on the detailed specification of the Parent Application—which is repeated and set forth at length below. Specific embodiments of the Claims set forth in this Continuation Application are summarized below:

A communications network is established where devices are assigned either a static or random unique device identifier; where devices may be configured to be in public or private mode; and where devices are in public mode, they may detect, discover, authenticate and communicate directly with each other, based on such attributes as interests, proximity, or location within a specified zone (such a network herein an "RF Aware Network", and such devices herein, "RFA Devices"). In certain networks (separately herein, an "SST Aware Network"), devices in public mode may use applicant's sixth-sense technology (as described in the Parent Application) to authenticate and communicate with each other (such devices herein, "SSTA Devices"; and RFA Devices and SSTA Devices jointly herein, "Network Aware Devices", or simply "NADs").

Network Aware Devices can advertise or subscribe to services based on proximity, interests or other attributes. They can indicate their preference to detect replies only from closer devices or from all NADs by setting parameters. Publish messages make a service discoverable by other devices in the same cluster. A service can broadcast its availability continuously (unsolicited) or only when requested by an active subscriber (solicited). For example, a RFA-certified printer could broadcast its availability continuously to nearby devices.

Subscribe messages sent to devices in a cluster indicate that the devices should transmit publish messages when specific criteria are met. Active subscribe messages look for solicited publishers. Passive subscribe messages look for the continuously broadcast unsolicited publishers. By using matching filter parameters, Network Aware Devices can specify in more detail the services being sought or offered. Also, service response filters enable NADs to respond to each other (or not) based on their static or random service ID or other variable identification information, and whether they are included or excluded from a list defined in attributes.

Applications can follow up with services on other Network Aware Devices. This is how a service or application can determine which people at a conference trigger an alert on a NAD, or whether to display information about an exhibit as the NAD passes it in a museum.

Sixth-Sense Technology

This Brief Summary of the SST Invention is the same as set forth in the Parent Application, and thus contains no new matter.

For wired, wireless and other communications, we have conceived, created and developed new communications methods for people, businesses and organizations ("participants") to search, sense and become aware of what others are interested in (and/or with whom they want or are willing to communicate) and to connect those people in private and anonymous communications based on their shared interests and thoughts.

A shorthand description of this new invention is as follows:

(a) it performs a search/discovery engine function in the fields of communications, thoughts and interests, similar to the following familiar tools: what an Internet search engine does for URL addresses and content; what a telephone directory does for phone numbers; what a television guide does for broadcast and cable television;

(b) it enables sensing, alerting, and becoming aware of such other persons and/or devices;

(c) it enables the delivery and completion of the sender's communications and stories, privately and anonymously, with unknown recipients and devices selected by the sender; and (d) the sixth sense discovery invention performs both "push" and "pull" functions.

One aspect of the present SST invention relates to creating and providing people with the ability to search, "sense" and be alerted to unknown third parties with whom they want or are willing to communicate ("recipients"), and engage directly in real-time communications with such unknown recipients, without knowing the identity, address, contact information or location of the recipients (herein, "unknown recipients").

Another aspect of the present SST invention also relates to creating and providing people with the ability to search, sense and be alerted to what others are interested in (and/or with whom they want or are willing to communicate) and to connect those people in private (or public) and anonymous communications based on their shared interests and thoughts.

Another aspect of the present SST invention also relates to creating and providing participants, groups, businesses, organizations and other parties with the means to search, discover and be alerted to what other people are interested in, and to deliver, share and learn to, with and from new and unknown recipients, through the exchange of voice, video, data and multi-media.

A first embodiment—of the single or multi-user push operation for our sixth-sense discovery invention—relates to creating and providing people with the ability to send real-time content to one or more others who might be interested in a particular topic. An example of this embodiment is where a person or organization wants to direct in real-time content (e.g., in the form of a message or voice alert) to one or more others who might be interested in a particular political or social cause. The person or organization would use a device and communications network enhanced by the invention to discover and become aware of who is interested in receiving such content, and then send the desired content, privately and anonymously, to all unknown recipients chosen by the sender.

A second embodiment—of the single or multi-user pull operation of our sixth-sense discovery invention—relates to creating and providing people with the ability to learn more about a particular topic. An example of this embodiment is where a person wants to learn more about "gay marriage". While attending a business conference, his device (enhanced with our invention) senses that a gay rights activist is nearby, and sends him an alert. The participant checks his device; learns that Lloyd C. Blankfein, the chief of Goldman Sachs and national corporate spokesperson for The Human Rights Campaign (THRC), is sitting across the aisle; texts Mr. Blankfein to set up an inquiry or even a meet and greet; and then at Mr. Blankfein's request, receives a full report from THRC reviewing both sides of the gay marriage debate.

A third embodiment relates to creating and providing new communications methods for people, groups, businesses, organizations and other parties to search, discover and become aware of what other people are interested in, and to deliver, share and learn, with and from new and unknown recipients, through the exchange of voice, video, data and multi-media. An example of this embodiment is where a person desires to find out what interests others, inclusive of everyone from the newcomer at school, the person across town, or someone halfway around the globe. People will get a sense of and be alerted to the other guy's 'story', and be able to share voice, pictures, video and data content based on common interests, creating ties that bind, and bringing people together.

A fourth embodiment relates to creating and providing businesses and people, and governments, institutions, and other organizations, with:
  new methods for searching and prospecting for new customers and contacts,
  new methods for distributing and selling new and additional products to existing and new customers,
  new methods for conducting market research, consumer surveys, surveys and focus groups for new product features, new products, product development, and research and development,
  new methods for forecasting demand and creating, maintaining and improving operations and supply-chain management, and
  new methods for conducting global, supra-national, national, regional and census, public health and other data-gathering; public policy development; dissemination of emergency alerts, public-health news and other information; distribution of benefits; and political outreach, recruitment, opinion polls, advocacy and other political activities.

An example of this embodiment is where a businesses or organization wants to discover, become aware of, and/or engage new customers and prospects for their products, services and causes. Another example of this embodiment is where a media content producer would use our new communications methods to discover and become aware of which groups of anonymous consumers are or might be interested in their content; send those people a message or alert that their content is available for purchase, streaming or download; and then complete the delivery of their content to such unknown people or devices—without needing to negotiate with a cable television company or other digital distributor, for example, terms and conditions, including without limitation such terms as: bundled-service package restrictions and/or other conditions; distribution fees and/or transaction commissions or fees; or digital rights management restrictions. Freed of such restrictions and costs, vendors will receive the following benefits:

(i) greater adjusted gross margins, which enable both lower consumer prices and greater business reinvestment;

(ii) by gaining direct access to customers and prospects: (a) new ideas for new products, features, and improvements to existing products, and (b) greater customer satisfaction and loyalty;

(iii) lower costs resulting from reduced license fees and similar expenses relating to license/rental of third-party 'house lists' and other prospecting databases; and (iv) other benefits resulting from avoidance of competitive restrictions dictated by third parties who control access to the customer and prospect of the vendor's products, services and/or causes.

A fifth embodiment relates to creating and providing consumers with new methods for purchasing products or services. An example of this embodiment is where an individual wants to remain anonymous throughout the entire purchase process, from research and screening, to referrals and recommendations, to closing the deal. Another example of our searching, sensing, discovery, alerting, and delivery method is where a novice consumer wants to start a reggae musical collection, so she uses our new communications method to identify an industry expert, solicit and procure their recommendations, and purchase selected digital music directly from the artists' mobile website, all privately and anonymously—without needing: (i) an account; (ii) membership for distributors like iTunes or Spotify; or (iii) searches of websites or Internet URLs.

In some embodiments, a method is disclosed of selectively communicating with one or more other devices whose identification information is unknown, the method comprising launching a client application on a device, wherein the client application enables communication with other devices whose identification information is unknown, identifying and locating other devices listing a searched-for identified attribute (such as at least one of the user's professional, associational, personal, physical, social, athletic, recreational, hobby and other interests and attributes), or any other data associated with the device or its user, that the second client application compiles; obtaining information regarding the other devices listing such searched-for attribute; compiling the information regarding the other devices listing the searched-for attribute to enable selection of at least one device to initiate communication using service messages, tags or tokens or other identifiers (jointly herein, "Variable Identifiers"); displaying a selection of the at least one device from the compiled information of the other devices listing such searched-for attribute; enabling privacy preferences for the device, wherein the privacy preferences enable the device to provide variable identification information to the at least one other device; enabling the client application on the device to specify whether the Variable Identifier is associated with private content, wherein the private content is sent only to the at least one other device; and sending the private content from the device to the at least one other device.

In some embodiments, a method is disclosed of selectively communicating with one or more other devices whose identification information is unknown, the method comprising launching a client application on a device, wherein the client application enables communication with other devices whose identification information is unknown; identifying an attribute (such as at least one of the user's gender, professional, associational, personal, physical, social, athletic, recreational, hobby and other interests and attributes), or any other data associated with the device or its user, that the device or its user wants to make known to other devices and users whose identification is unknown, which attribute is compiled by the first client application; identifying at least one criterion (such as attribute, location, time of day, date, etc) for sharing such attribute with at least one other user or device, which criterion is compiled by the first client application; identifying and locating other devices based on such one or more criteria; obtaining information regarding the other devices meeting such criteria; compiling the information regarding the other devices meeting such criteria to enable selection of at least one device to initiate communication using service messages, tags or tokens or other identifiers (jointly herein, "Variable Identifiers"); displaying a selection of the at least one device from the compiled information of the other devices meeting such criteria; enabling privacy preferences for the device, wherein the privacy preferences enable the device to provide variable identification information to the at least one other device; enabling the client application on the device to specify whether the Variable Identifier is associated with private content, wherein the private content is sent only to the at least one other device; and sending the private content from the device to the at least one other device.

In some embodiments, a method is disclosed of selectively communicating with one or more other devices whose identification information is unknown, the method comprising launching a client application on a device, wherein the client application enables communication with other devices whose identification information is unknown; identifying the other devices based on selected criteria using the client application, wherein the selected criteria comprise both (i) a searched-for identified attribute (such as at least one of the user's professional, associational, personal, physical, social, athletic, recreational, hobby and other interests and attributes), or any other data associated with the device or its user, and (ii) one or more searched-for locations or zones (jointly herein, a "zone"); obtaining attribute and/or other data and information regarding the other devices located in the searched-for zone; compiling such information regarding the other devices located in the searched-for zone to enable selection of at least one device to initiate communication using service messages; displaying a selection of the at least one device from the compiled information of the other devices located in the searched-for zone; enabling privacy preferences for the device, wherein the privacy preferences enable the device to provide variable identification information to the at least one other device; enabling the client application on the device to specify whether the Variable Identifier is associated with private content, wherein the private content is sent only to the at least one other device; and sending the private content from the device to the at least one other device.

In some embodiments, a device for selectively communicating with one or more other devices whose identification information is unknown, the device comprising an interface that is configured to communicate with the one or more other devices, and a client application that is configured to communicate with the interface to search for at least one of the one or more other devices based on selected criteria specified in the client application and to compile information obtained from the one or more other devices; the client application further configured to send a message to one or more other devices selected from the compiled information, and to enable privacy preferences for the device, wherein the privacy preferences enable the device to provide variable identification information to the at least one other device, as well as to enable the client application to specify whether the variable identification information is associated with private content, so that the private content is sent only to the at least one other device; and the device interface configured to send the private content from the device to the at least one other device.

In some embodiments, a method of selectively communicating between devices when identification information used to contact a device is unknown, the method comprising receiving, at a remote processing server, registration information from a first device; creating user identification information for the first device and associating the user identification information with the registration information; determining attributes and criteria for the first device and associating the criteria in the database with the user identification information of the first device; receiving, at the remote processing server, a second registration from at least one other device; organizing information from the first device and the at least one other device in a database on the remote processing server; determining attributes and criteria for the at least one other device and storing in the database; receiving a service message, at the remote processing server, from the first device, wherein the service message comprises content and user identification information; searching the database using the criteria selected by the first device to locate at least one other device that is within parameters specified by the first device; obtaining information for the at least one other device and processing the service message to send to the at least one other device; and sending a processed service message including the content of the service message to the at least one other device.

BRIEF DESCRIPTION OF THE DRAWINGS

This Brief Description of the Drawings is the same as set forth in the Parent Application, and thus contains no new matter.

FIG. 1 illustrates communications devices that provide searching, discovering, sensing, sharing, sending and receiving stories, content, interests and data among known and unknown people and devices, including communication to and with recipients whose traditional identification information is unknown in accordance with certain embodiments. A method and system for searching, sensing, discovering, enabling awareness, alerting, screening, sharing, sending, receiving, buying, selling, and otherwise transmitting stories, content, interests, data, goods and services among known and unknown devices in a communication network.

DETAILED DESCRIPTION

This Detailed Description of the Invention is the same as set forth in the Parent Application, and thus contains no new matter.

Methods and systems are provided for searching, sensing, discovering, sharing, sending and receiving stories, content, interests and data among known and unknown people and devices in a communication network, in accordance with certain embodiments.

Platt et al teach us how to communicate without traditional identification information or communication methods, both directly between devices, U.S. Pat. No. 8,396,489, and with the aid of a server, U.S. Pat. No. 8,396,490 (the "Related Inventions").

But the Related Inventions do not teach how to search, discover, sense, share, send and receive stories, content, interests and data among known and unknown people and devices. For example, you may want to "know the story" of, or learn something about, an unknown person across the street, across the stadium, or on the other side of the world—without sending a message and awaiting a response. Another example is where you may want to purchase a new product or service, but don't know a business that sells it—and you don't have access to the Internet or don't have the time to conduct a web search. Another instance could be where business may want to find new customers or prospects—without renting or buying a list of names. A different example could be where an artist or producer may want to distribute its artistic creation—without using a digital distributor like Comcast or iTunes. In order to provide this type of communication among and with people, groups, and devices whose traditional identification information is unknown, various systems, methods, and apparatus are disclosed.

Reference will now be made in detail to embodiments, an example of which is illustrated in the accompanying drawing. In the following detailed description, numerous specific details are set forth in order to provide a thorough understanding of the present invention. However, it will be apparent to one of ordinary skill in the art that the present invention may be practiced without these specific details. In other instances, methods, procedures, components, and circuits taught by the Related Inventions—for both (a) communications without traditional identification information, and (b) communication methods, both directly between devices and with the aid of a server—have not been described in detail so as not to unnecessarily obscure aspects of the embodiments.

FIG. 1 illustrates communications devices that provide searching, discovering, sensing, sharing, sending and receiving stories, content, interests and data among known and unknown people and devices, including communication to and with recipients whose traditional identification information is unknown in accordance with certain embodiments.

FIG. 1 illustrates a portable, mobile or static-location electronic device, according to some embodiments of the invention, including, by way of illustration and not limitation, a server, router, switch, personal computer, laptop, notebook, mobile devices such as a tablet, smartphone, and wearable computers such as shoes, glasses, or implanted chips. The device 100 includes a memory 102, a memory controller 104, one or more processing units (CPU's) 106, a peripherals interface 108, RF circuitry 112, audio circuitry 114, a speaker 116, a microphone 118, an input/output (I/O) subsystem 120, a touch screen 126, other input or control devices 128, and an external port 148. These components communicate over the one or more communication buses or signal lines 110. The device 100 can be any electronic device, including but not limited to a desktop or laptop computer, a landline telephone, handheld computer, a tablet computer, a mobile phone, a media player, a personal digital assistant (PDA), or the like, including a combination of two or more of these items. It should be appreciated that the device 100 is only one example of an electronic device 100, and that the device 100 may have more or fewer components than shown, or a different configuration of components. The various components shown in FIG. 1 may be implemented in hardware, software or a combination of both hardware and software, including one or more signal processing and/or application specific integrated circuits.

The memory 102 may include high speed random access memory and may also include non-volatile memory, such as one or more magnetic disk storage devices, flash memory devices, or other non-volatile solid state memory devices. In some embodiments, the memory 102 may further include storage remotely located from the one or more processors 106, for instance network attached storage accessed via the RF circuitry 112 or external port 148 and a communications network (not shown) such as the Internet, intranet(s), Local Area Networks (LANs), Wide Local Area Networks (WLANs), Storage Area Networks (SANs) and the like, or any suitable combination thereof. Access to the memory 102 by other components of the device 100, such as the CPU 106 and the peripherals interface 108, may be controlled by the memory controller 104.

The peripherals interface 108 couples the input and output peripherals of the device to the CPU 106 and the memory 102. The one or more processors 106 run various software programs and/or sets of instructions stored in the memory 102 to perform various functions for the device 100 and to process data.

In some embodiments, the peripherals interface 108, the CPU 106, and the memory controller 104 may be implemented on a single chip, such as a chip 111. In some other embodiments, they may be implemented on separate chips.

The RF (radio frequency) circuitry 112 receives and sends electromagnetic waves. The RF circuitry 112 converts electrical signals to/from electromagnetic waves and communicates with communications networks and other communications devices via the electromagnetic waves. The RF circuitry 112 may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. The RF circuitry 112 may communicate with the networks, such as the Internet, also referred to as the World Wide Web (WWW), an Intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Long Term Evolution (LTE/4G). Global System for Mobile Communications (GSM), Enhanced Data GSM Environment (EDGE), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email, instant messaging, Short Message Service (SMS) and/or Multimedia Messaging Service (MMS)), or any other suitable communication protocol, including communication protocols not yet developed as of the filing date of this document.

The audio circuitry 114, the speaker 116, and the microphone 118 provide an audio interface between a user and the device 100. The audio circuitry 114 receives audio data from the peripherals interface 108, converts the audio data to an electrical signal, and transmits the electrical signal to the speaker 116. The speaker converts the electrical signal to human-audible sound waves. The audio circuitry 114 also receives electrical signals converted by the microphone 116 from sound waves. The audio circuitry 114 converts the electrical signal to audio data and transmits the audio data to the peripherals interface 108 for processing. Audio data may be may be retrieved from and/or transmitted to the memory 102 and/or the RF circuitry 112 by the peripherals interface 108. In some embodiments, the audio circuitry 114 also includes a headset jack (not shown). The headset jack provides an interface between the audio circuitry 114 and removable audio input/output peripherals, such as output-only headphones or a headset with both output (headphone for one or both ears) and input (microphone).

The I/O subsystem 120 provides the interface between input/output peripherals on the device 100, such as the touch screen 126 and other input/control devices or components, such as device-control sensors 128, and the peripherals interface 108. The I/O subsystem 120 includes a touch-screen controller 122 and one or more input controllers 124 for other input or control devices. The one or more input controllers 124 receive/send electrical signals from/to other input or control devices 128. The other input/control devices 128 may include physical buttons (e.g., push buttons, rocker buttons, etc.), dials, slider switches, sticks, and so forth.

The touch screen 126 provides both an output interface and an input interface between the device and a user. The touch-screen controller 122 receives/sends electrical signals from/to the touch screen 126. The touch screen 126 displays visual output to the user. The visual output may include text, graphics, video, and any combination thereof. Some or all of the visual output may correspond to user-interface objects, further details of which are described below.

The touch screen 126 also accepts input from the user based on haptic and/or tactile contact. The touch screen 126 forms a touch-sensitive surface that accepts user input.

In some embodiments, in addition to the touch screen, the device 100 may include a touchpad (not shown) for activating or deactivating particular functions. In some embodiments, the touchpad is a touch-sensitive area of the device that, unlike the touch screen, does not display visual output. The touchpad may be a touch-sensitive surface that is separate from the touch screen 126 or an extension of the touch-sensitive surface formed by the touch screen 126.

The device 100 also includes a power system 130 for powering the various components. The power system 130 may include a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the software components include an operating system 132, a communication module (or set of instructions) 134, a contact/motion module (or set of instructions) 138, a graphics module (or set of instructions) 140, a user interface state module (or set of instructions) 144, and one or more applications 146, including a VII Client 149 and an SST Client (as each term is defined below) 150.

The operating system 132 (e.g., Darwin, RTXC, LINUX, UNIX, OS X, iOS, ANDROID, WINDOWS, or an embedded operating system such as VxWorks) includes various software components and/or drivers for controlling and managing general system tasks (e.g., memory management, storage device control, power management, etc.) and facilitates communication between various hardware and software components.

The communication module 134 facilitates communication with other devices over one or more external ports 148 and also includes (i) various software components for handling data received by the RF circuitry 112 and/or the external port 148, and (ii) a device interface and client application that enable communications with Variable Identifier information (jointly herein, (a "VII Client") 149—as taught by the Related Inventions, in addition to and independently of email addresses, telephone numbers, social network or social media registration, or instant messaging handles, aliases or addresses. The external port 148 (e.g., Universal Serial Bus (USB), FIREWIRE, etc.) is adapted for coupling directly to other devices or indirectly over a network (e.g., the Internet, wireless LAN, etc.).

The contact/motion module 138 detects contact with the touch screen 126 or interaction with other input/control devices 100, in conjunction with the touch-screen controller 122. The contact/motion module 138 includes various software components for performing various operations related to detection of contact with the touch screen 122, such as determining if contact has occurred, determining if there is movement of the contact and tracking the movement across the touch screen, and determining if the contact has been broken (i.e., if the contact has ceased). Determining movement of the point of contact may include determining speed (magnitude), velocity (magnitude and direction), and/or an acceleration (including magnitude and/or direction) of the point of contact. In some embodiments, the contact/motion module 126 and the touch screen controller 122 also detects contact on the touchpad.

The graphics module 140 includes various known software components for rendering and displaying graphics on the touch screen 126. Note that the term "graphics" includes any object that can be displayed to a user, including without limitation text, web pages, icons (such as user-interface objects including soft keys), digital images, videos, animations and the like.

The device includes an application deploying sixth-sense technology (SST), known as the SST Client 150, which enables the discovery, alerting, and delivery of all forms (e.g., voice, video, data, multi-media) of global content and commerce among devices and people based on such sixth-sense communications capabilities.

The one or more applications 146 can include any applications installed on the device 100, including without limitation, a VII Client, an SST Client, a browser, address book, contact list, email, instant messaging, word processing, keyboard emulation, widgets, JAVA-enabled applications, encryption, digital rights management, voice recognition, voice replication, location determination capability (such as that provided by the global positioning system (GPS)), a music player (which plays back recorded music stored in one or more files, such as MP3 or AAC files), etc.

In some embodiments, the device may include a hardware GPS unit 151 which determines current location based on current GPS satellite locations and/or cell-tower positioning.

In some embodiments, the device 100 may include the functionality of an MP3 player, such as an iPod (trademark of Apple Computer, Inc.). In some embodiments, the device 100 is a device where operation of a predefined set of functions on the device is performed exclusively through the touch screen 126 and, if included on the device 100, the touchpad.

The predefined set of functions that are performed exclusively through the touch screen and the touchpad include navigation between user interfaces. In some embodiments, the touchpad, when touched by the user, navigates the device 100 to a main, home, or root menu from any user interface that may be displayed on the device 100. In such embodiments, the touchpad may be referred to as a "menu button." In some other embodiments, the menu button may be a physical push button or other physical input/control device instead of a touchpad.

User Attributes and User Profiles

The device 100 may have a single or plurality of user attributes and user profiles. These attributes and user profiles are created, set or maintained by each of one or more individuals using the device, or by the device itself applying an algorithm or other software program running on or deployed by the device (such individual, individuals or device creating, set or maintained the attributes or profile herein, a user) via the SST Client 150. User attributes may include, by way of example and not by way of limitation, one or more of the user's professional, associational, personal, physical, social, athletic, recreational, hobby, locational, geospatial, and other interests, preferences, and attributes, or any other data associated with the device or its user (collectively herein, "Attributes"). A user might set up one or more user profiles (each of which might contain or prioritize different attributes or topics) (herein, "Profiles"), such as a work profile, a hobby profile, a family profile, and a social profile. These Attributes and Profiles are stored in one or more databases that, using the SST Client 150, can be named, indexed, searched for, retrieved, edited, merged, grouped, terminated or otherwise configured by one or more users who have authorized access to the device and the specific SST Client.

One embodiment of the present SST invention relates to creating and providing people (herein, "seekers") with the ability to search, "sense" and be alerted to unknown third parties with whom they want or are willing to communicate ("recipients"), wherein both seekers and recipients are using devices equipped and operating both an SST Client and a VII Client—and engage directly in real-time communications with such unknown recipients, without knowing the identity, address, contact information or location of the recipients (herein, "unknown recipients").

Using features of an SST Client on the device 100, a user, or 'seeker', may search, detect, discover, alert and sense unknown recipients and their unknown devices with Attributes lying within specified parameters selected by the user of the first device—which Attributes of the at least one third-party device 200 might, but are not required to, overlap in whole or in part with the Attributes of the device 100 of the first user. The parameters might include, for example, third-party devices within one or more certain or general geographic location(s) or zone(s) (jointly herein, a "zone") being used by a person with a specified age range with a professional or academic interest in certain topics or fields.

Seekers can configure the SST Client on their device 100 to search for, identify, alert, and display when it has detected the searched-for attribute(s) and parameters of users, or 'recipient' of the at least one third-party device 200, and, using the VII Client 149 on each device, initiate contact and communications with such third party device, even when its traditional identification information is unknown.

Another embodiment creates and providers users, or seekers, with the ability to search, sense and be alerted to what other users (herein, a collaborator) are interested in, and/or with whom they want or are willing to communicate; and to connect those people in private (or public) and anonymous communications based on their shared interests and thoughts—where each device is equipped with and operating an SST Client and a VII Client.

For example, a collaborator might configure the SST Client on her device 100 to specify that she is interested in topics A, B and C; and is willing to communicate about topics B1 and C2 with other unknown seekers who are affiliated with the post-secondary academic community in a specified geographic region. That communication interest would be sensed by the SST Client on the device 200 of a third-party seeker with such an academic affiliation interested in communication topics B1 and C2, and trigger an alert on such device. Upon checking the alert and reading the related display, the seeker would use the SST Client on his device 200 to compose and send a private and anonymous email or other message to the collaborator, notifying her of his interest in communication topics B1 and C2. From there, the collaborator and seeker would engage in such further communications and exchange of information as they deem suitable; maintaining such privacy and anonymity as each desires, using the communications capabilities of the VII Client, as integrated with the SST Client.

A third embodiment relates to creating and providing participants, groups, businesses, organizations and other parties with the means to search, discover and be alerted to what other people are interested in, and to deliver, share and learn to, with and from new and unknown recipients, through the exchange of voice, video, data and multi-media.

For example, the product manager (herein, a seeker) of a major snowboard brand might want to learn what new tricks riders are trying in diverse urban and backwoods environments, and product enhancements and new performance criteria suggested by rider usage. Random riders (each, a responder) might configure the SST Client on his device 100 to specify that she is interested in snowboarding, and is willing to communicate about new tricks, urban riding, and extreme terrain with unknown persons and businesses interested in snowboarding. That communication interest would be sensed by the SST Client on the device 200 of the seeker, and trigger an alert on such device. Upon checking the alert and reading the related display, the seeker would use the SST Client on his device 200 to compose and send a private and anonymous email or other message to the responder, notifying him of his interest in new snowboarding tricks, urban riding, and extreme terrain. From there, responder and seeker would engage in such further communications and exchange of information as they deem suitable, such as the responder sending the seeker a secure link to a private video of his extreme rides down urban sidewalk steps and down gnarly mountain chutes; maintaining such privacy and anonymity as each desires, using the communications capabilities of the VII Client, as integrated with the SST Client.

Another example of this embodiment is where a pearson (user 1) desires to find out what interests others (user 2 et seq), inclusive of everyone from the newcomer at school, the person across town, or someone halfway around the globe. Using devices 100/200 equipped with and operating an SST Client and a VII Client, each of user 1 and user 2 configure their STT Client selecting to disclose to the public at large certain attributes. The device 100 of user 1 discovers such attributes of User 2, and displays them on user 1's device. User 1 thus gets a sense of and be alerted to the other guy's 'story', and be able to share voice, pictures, video and data content based on common interests, creating ties that bind, and bringing people together.

A fourth embodiment—illustrating the push operation of the SST Client—relates to creating and providing people with the ability to send real-time content to one or more others who might be interested in a particular topic.

An example of this embodiment is where a person or organization (herein, a 'broadcaster') wants to direct in real-time content (e.g., in the form of a message or voice alert) to one or more others ("recipients") who might be interested in a particular political or social cause. The device (or communications network) of both broadcaster and recipient would be equipped with and running an SST Client and VII Client. A Broadcaster can configure the SST Client on their device 100 to search for, identify, alert, and display specific attribute(s) and parameters in third-party devices. Others users of such third party devices 200/300 would configure their respective SST Client indicating various interests that they have and any time/place restrictions on communications with others regarding such interests. The device of the broadcaster discovers those people and groups who are interested in receiving the searched-for content, displays an alert when it has detected the searched-for attribute(s) and parameters of recipient(s) using at least one third-party device 200, and, using the VII Client 149 on each device, initiates contact and communications with such third party device, and then send the desired content, privately and anonymously, to all unknown recipients chosen by the broadcaster.

Another embodiment—illustrating the pull operation of our sixth-sense discovery invention—relates to creating and providing people with the ability to learn more about a particular topic.

An example of this embodiment is where a person (a seeker) wants to learn more about "gay marriage". She configures the SST Client on her device 100 to indicate that one of her interests is gay marriage, and a willingness to communicate with unknown third parties during business hours or when she is away from home. Separately, a prominent gay rights activist (an Activist) has configured the SST Client on his device 200 with comparable settings, together with his official role with a national human rights organization. Both devices are equipped with a VII Client. While attending a business conference, the seeker's device 100 senses that the device 200 of the Activist is nearby, and displays an alert. The seeker checks her device; learns that the national corporate spokesperson for The Human Rights Campaign (THRC), is sitting across the aisle; and using the VII Client 149 on each device, sends a text, privately and anonymously, to the Activist, seeking to set up an inquiry or even a meet and greet.

Without exchanging or revealing email addresses, phone numbers or other contact data, the seeker and Activist are able to exchange messages, and then, the Activist arranges for THRC to send seeker a full report reviewing both sides of the gay marriage debate.

A sixth embodiment relates to creating and providing businesses and people, and governments, institutions, and other organizations, with:
  new methods for searching and prospecting for new customers or contacts,
  new methods for distributing and selling new and additional products to existing and new customers,
    new methods for engaging in any or all forms of commercial transactions, including without limitation sharing, sending, receiving, procuring, distributing, streaming, purchasing, subscribing, leasing, renting, borrowing, licensing, selling, or transmitting products, services or content (all such commercial transactions collectively, "Commercial Sale"),
    new methods for conducting market research, consumer surveys, surveys and focus groups for new product features, new products, product development, and research and development,
  new methods for forecasting demand and creating, maintaining and improving operations and supply-chain management, and
  new methods for conducting global, supra-national, national, regional and census, public health and other data-gathering; public policy development; dissemination of emergency alerts, public-health news and other information; distribution of benefits; and political outreach, recruitment, opinion polls, advocacy and other political activities.

An example of this embodiment is where a businesses or organization (a business) wants to discover and become aware of, and direct marketing content to, new customers and prospects (jointly, a consumer) for their products, services and causes. The business equips its customer-facing staff with tablets 100 running an SST Client and VII Client. Each staff member configures their SST Client identifying their expertise in specific categories of business products; ability to speak one or more languages; availability to engage in consumer communications during various intervals throughout the day. Separately, consumers holding devices 200/300 running SST and VII Clients configure their SST Client noting their interest in certain product categories, and their desire to text or call in Spanish at specified times of day or when present in certain locations (e.g., at home, in-store, or near-store). A Spanish-speaking business staff member with relevant product knowledge receives an alert on his device 100 of such consumer's interest, and is able, using the VII Client on his device, initiate a private and anonymous communication with such consumer, and then, at the consumer's convenience and regardless of location, renew the private and anonymous communication with the consumer, through and including the close of the sale. Using this embodiment, businesses will be able to sell direct to the public, without having to incur distribution costs, for example to distributors and retailers, or to digital distributors (e.g., Amazon).

Another example of this embodiment is where a media content producer (a producer) wants to discover and become aware of which groups of anonymous consumers (a viewer) are or might be interested in their content. The producer equips its server 100 running an SST Client and VII Client, and configures their SST Client listing and indexing their library of movies, videos and ads, along with other information such as duration, language, and pertinent pricing (if any). Separately, viewers holding devices 200/300 running SST and VII Clients configure their SST Client noting their interest in certain movie genres, video categories, and ad topics, along with any pertinent time and location parameters restricting when and where they are willing to receive and view such content. The producer's server 100 receives notice of such viewer's interest, and is able, using the VII Client on the server, establish a private and anonymous communication with such viewer, informing her that the content is available for purchase, streaming or download; and then complete the delivery of desired content to the anonymous viewer in a private communication.

A seventh embodiment relates to creating and providing consumers with new methods for purchasing products or services.

An example of this embodiment is where an individual (a driver) wants to remain anonymous throughout the entire process of purchasing a car, from research and screening, to referrals and recommendations, to closing the deal. Using a smartphone device 100, the driver configures the SST Client to indicate his interest in buying a new or used car with various attributes and that is available for inspection, test drive and delivery within a designated mileage radius from his place of work. Separately, car dealers, car-search platforms (e.g., Autotrader), and private sellers (jointly, sellers) configure the SST Clients on their computers 200 identifying the attributes (including, e.g., pictures and videos) of their inventory of cars for sale; while car-service organizations (e.g., CarFax; Consumer Reports magazine; Car & Driver magazine; state vehicle registration bureaus)(jointly, resource groups) configure the SST Clients on their servers 300 to provide access to car reviews, car specifications, and vehicle information. The driver's phone 100 discovers from sellers' computers 200 (using SST and VII Clients) car(s) meeting the driver's criteria and any pertinent available reviews, etc from resource groups, and displays an alert on his phone. When he taps on the alert, the SST Client opens and displays links to the sellers' car listings and resource groups' car reviews, etc. From there, the driver and sellers and/or resource groups would engage in such further communications and exchange of information as they deem suitable; maintaining such privacy and anonymity as each desires, using the communications capabilities of the VII Client, as integrated with the SST Client.

Another example of our searching, sensing, discovery, alerting, and delivery method for purchasing a product or service is where an inexperienced individual (a listener) wants to start a reggae musical collection. She configures the SST client on her tablet or MP3 player 100 to indicate her reggae interest and solicit names of top reggae performers, critics and bloggers. Separately, at least one reggae performer, critic or blogger (a specialist) configures the SST Client on each of his computer 200 and music-storage server 300 identifying: (i) attributes both of reggae music (including any accompanying recommendation and referrals) stored on the server and referencing playlists of various collections comprised of single and multiple artists for first-time reggae followers, and of persons with whom they are willing to consult (while preserving the privacy of their contact information); and any personal temporal, location and other parameters restrictions on the devices that might sense and communicate with such specialist. The listener's device 100 discovers from specialist's computer 200 and server 300 (using SST and VII Clients) music and any recommendations or referrals meeting the listener's criteria and displays an alert on her phone. When she taps on the alert, the SST Client opens and displays links to the specialist. From there, the listener and specialist would engage in such further communications and exchange of information as they deem suitable; maintaining such privacy and anonymity as each desires, using the communications capabilities of the VII Client, as integrated with the SST Client.

In an eighth embodiment, a user (an initiator) can selectively communicate about desired topics with known or unknown people (a recipient) possessing certain characteristics who are using one or more other devices whose identification information is unknown. Using device 100 configured with an SST Client, the initiator launches the SST Client, and identifies an attribute or any other data associated with the device or its user, that he wants to make known to other devices and users whose identification is unknown, which attribute is compiled by the SST Client; the VII Client on the first device 100 enables communication with other devices 200 (also deploying a VII Client) whose identification information is unknown; the SST Client on the first device searches for and identifies at least one criterion (such as attribute, location, time of day, date, etc) for sharing such attribute with at least one other user or device deploying an SST Client, which criterion is compiled by the first SST Client; the SST Client running on the first device identifies and locates other devices based on such one or more criteria; obtains information regarding the other devices meeting such criteria; compiles the information regarding the other devices meeting such criteria to enable selection of at least one device to initiate communication using the VII Client on the first device; and displays a selection of the at least one device from the compiled information of the other devices meeting such criteria. Using the SST Client on the first device 100, the initiator selects the at least one other device 200 either with which he wants to communicate on a desired topic or which is being used by a person with the desired characteristics, and then using privacy preference settings within the SST Client on the first device 100, chooses whether he wants to preserve the privacy of his contact information; reveal his real name or location; or open a private 1:1 or public communication with such selected recipient or device 200; wherein the privacy preferences enable the device to provide variable identification information to the at least one other device; enables the VII Client on the first device to specify whether the Variable Identifier is associated with private content, wherein the private content is sent only to the at least one other device; and sends the private content from the first device to the at least one other device.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

We claim:

1. A communications network method enabling communications by, among and to devices in a specified geographic zone, the method comprising:

For each network device in the specified geographic zone, use of a variable identification information software or firmware client to assign a unique device identifier (ID), selected by using either:

generation of a static ID ("S-ID") based on at least one item from a set comprised of at least one of the following identifiers ("VII") associated with the network device (including its software and firmware): a MAC address, IP address, serial number, other device identifying information, attribute, service message, tag, token, vendor device identifier, advertising device identifier, other datum, and other variable identification information, or generation of a random or dynamically changing ID ("R-ID") based on at least one VII associated with the network device;

Using a sixth-sense ("SST") software or firmware client on a first network device to detect at least one attribute ("SFA") from a set comprised of at least one of the following data associated with a recipient network device ("recipient device"): a searched-for interest, activity, attribute, characteristic, interest, preference, location, parameter, software, firmware, hardware component, promotion, service, product, VII, and other datum;

Using the VII client on the first network device to authenticate, inside or outside the specified geographic zone, the at least one recipient device based on either its S-ID or R-ID; and Using the VII client on the at least one recipient device to authenticate, inside or outside the specified geographic zone, any other network device based on either its S-ID or R-ID.

2. A communications network method described in claim 1, wherein at least one of the network devices may be configured to enable at least one of the following capabilities:

Be in public mode wherein the ID of such a network device ("aware device") is detectable by other network devices;

Using either its VII Client or SST Client, a first aware device can conduct, with respect to at least one recipient aware device ("affinity device"), at least one function from a set comprised of the following functions: search, detection, and authentication;

Search for at least one SFA associated with at least one affinity device;

Establish a data connection independent of existing telephone, Internet Protocol, Wi-Fi and other networks to share voice, video or data, using a peer-to-peer technology or an infrastructure connection;

Send an alert to at least one aware device;

Send an alert to at least one affinity device;

Receive an alert from at least one aware device;

Receive an alert from at least one affinity device;

Send a public broadcast message or other communication to at least one aware device;

Send a public broadcast message or other communication to at least one affinity device;

Receive a public broadcast message or other communication from at least one aware device;

Receive a public broadcast message or other communication from at least one affinity device;

Send a public broadcast message or other communication to at least one aware device based on at least one SFA of the said device;

Send a public broadcast message or other communication to at least one affinity device based on at least one SFA of the said device;

Receive a public broadcast message or other communication from at least one aware device based on at least one SFA of the said device;

Receive a public broadcast message or other communication from at least one affinity device based on at least one SFA of the said device;

Send a private message or other communication to at least one aware device;

Send a private message or other communication to at least one affinity device;

Receive a private message or other communication from at least one aware device;

Receive a private message or other communication from at least one affinity device;

Using a service communication filter ("SCF") in its SST client, send a private message or other communication to at least one aware device based on at least one SFA of the said device;

Using a SCF in its SST client, send a private message or other communication to at least one affinity device based on at least one SFA of the said device;

Using a SCF in its SST client, receive a private message or other communication from at least one aware device based on at least one SFA of the said device;

Using a SCF in its SST client, receive a private message or other communication from at least one affinity device based on at least one SFA of the said device;

Passively receive from at least one aware device at least one communication from a set comprised of at least one of the following: public broadcast search inquiry, alert, message and other communication;

Passively receive from at least one affinity device at least one communication from a set comprised of at least one of the following: public broadcast search inquiry, alert, message and other communication;

Passively receive at least one communication from a set comprised of at least one of the following—private search inquiry, alert, message and other communication—where such communication is based on at least one SFA of the recipient device identified by at least one sending aware device using a SCF in its SST client;

Passively receive at least one communication from a set comprised of at least one of the following—private search inquiry, alert, message and other communication—where such communication is based on at least one SFA of the recipient device identified by at least one sending affinity device using a SCF in its SST client; and Be in private mode, wherein the ID of the said private mode device is not detectable by other network devices.

3. A communications network method for communications by, among and to devices that enables searching and detecting attributes, characteristics, parameters or other data among known and unknown devices and their users, authenticating such devices and their users, message routing and directing private or anonymous targeted communications to and with specific devices and their users, and maintaining continuous or initiating repeat communications with and to such specific devices and their users, in each case regardless of initial or continued location of such devices or the proximity of such devices in a limited or designated physical area or zone, the method comprising:

Using a sixth-sense ("SST") software or firmware client on a first device to search for at least one attribute ("SFA") from a set comprised of at least one of the following data associated with a recipient network device ("recipient device"): interest, activity, attribute, characteristic, preference, location, parameter, software, firmware, hardware component, promotion, service, product, service message, tag, token, vendor device identifier, advertising device identifier, other datum, and other variable identification information;

Setting the SST client on the first device to enable at least one of the following capabilities:
 (i) discover at least one SFA of at least one recipient device;
 (ii) communicate with at least one recipient device whose identification information is unknown; and
 (iii) screen and locate at least one recipient device worldwide or within at least one geographic location or zone;

Enabling the SST client on the first device to obtain and compile on the first device at least one of the following data:
 (i) at least one item from a set comprised of at least one of the following data associated with at least one recipient device, including its software and firmware: SFA, information and other data; and (ii) at least one item from a set comprised of at least one of the following identifiers ("VII") associated with at least one recipient device (including its software and firmware): a MAC address, IP address, serial number or other device identifying information, attribute, service message, tag, token, vendor device identifier, advertising device identifier, other datum, and other variable identification information;

Applying at least one filter in the SST client of the first device to enable the first device to select at least one designated screened device, based on an analysis of items from a set comprised of at least one of the following identifiers associated with the at least one screened device: its SFA, VII and other compiled data;

Using a VII client on the first device to assign a unique device identifier (ID) to the at least one designated screened device based on a set comprised of at least one of the following identifiers associated with said designated screened device: its SFA, VII and other compiled data;

Using the VII client of the first device to authenticate and send a service message only to the at least one designated screened device, where either of the following conditions is also satisfied:

(i) the email address, public or private cryptography key, IM screen name, social media or Internet screen name, handle, alias, or avatar, phone number, MAC address, IP address or other contact information of the at least one designated screened device is not either known to the user of the first device or previously stored or used by either the first device, or any business, social or communications network to which the first device is registered; or (ii) the service message is authenticated by and/or from the first device using its VII client based on SFA, VII or compiled data of the at least one designated screened device; and without using email, public or private cryptography key, instant messaging (IM), text messaging, telephony or any other communications protocol or technique based on fixed endpoints where any of such contact information of the at least one designated screen device is either known to the user of the first device or previously stored or used by any of the first device, or any business, social or communications network to which the first device is registered; and Using the VII client or the SST client of the at least one designated screened device to authenticate the identity of the first device, based on an identifier from a set comprised of at least one of the ID, SFA, VII and other compiled data associated with the first device, regardless of whether either device remains in the zone in which initial contact and authentication between the devices was established.

4. A communications network method described in claim 3, wherein at least one of the network devices may be configured to enable at least one of the following capabilities:

Using the VII software or firmware client to assign an ID to at least one network device;

Setting privacy preferences on the first device, enabling the first device to send at least one of the following identifiers, from a set comprised of its SFA, VII and other compiled data, to at least one designated screened device;

Enabling the SST client on the first device to specify whether a service message is a private service message, wherein the private service message is sent only to, and is accessible only by, at least one designated screened device;

Be in public mode, wherein the ID of a network device ("public-mode device") is detectable by other network devices;

Using either its VII Client or SST Client, a first pubic-mode device can conduct, with respect to at least one recipient public-mode device ("affinity public-mode device"), at least one function from a set comprised of the following functions: search, detection, and authentication;

Search for at least one SFA associated with at least one affinity public-mode device;

Establish a data connection independent of existing telephone, Internet Protocol, Wi-Fi or other networks to share data, using a peer-to-peer technology or an infrastructure connection;

Send an alert to at least one public-mode device;

Send an alert to at least one affinity public-mode device;

Receive an alert from at least one public-mode device;

Receive an alert from at least one affinity public-mode device;

Send a public broadcast message or other communication to at least one public-mode device;

Send a public broadcast message or other communication to at least one affinity public-mode device;

Receive a public broadcast message or other communication from at least one public-mode device;

Receive a public broadcast message or other communication from at least one affinity public-mode device;

Send a public broadcast message or other communication to at least one public-mode device based on at least one SFA of the said device;

Send a public broadcast message or other communication to at least one affinity public-mode device based on at least one SFA of the said device;

Receive a public broadcast message or other communication from at least one public-mode device based on at least one SFA of the said device;

Receive a public broadcast message or other communication from at least one affinity public-mode device based on at least one SFA of the said device;

Send a private message or other communication to at least one public-mode device;

Send a private message or other communication to at least one affinity public-mode device;

Receive a private message or other communication from at least one public-mode device;

Receive a private message or other communication from at least one affinity public-mode device;

Using a service communication filter ("SCF") in its SST client, send a private message or other communication to at least one public-mode device based on at least one SFA of the said device;

Using a SCF in its SST client, send a private message or other communication to at least one affinity public-mode device based on at least one SFA of the said device;

Using a SCF in its SST client, receive a private message or other communication from at least one public-mode device based on at least one SFA of the said device;

Using a SCF in its SST client, receive a private message or other communication from at least one affinity public-mode device based on at least one SFA of the said device;

Passively receive from at least one public-mode device at least one communication from a set comprised of at least one of the following: public broadcast search inquiry, alert, message and other communication;

Passively receive from at least one affinity public-mode device at least one communication from a set comprised of at least one of the following: public broadcast search inquiry, alert, message and other communication;

Passively receive at least one communication from a set comprised of at least one of the following—private search inquiry, alert, message or other communication—based on at least one SFA of the recipient device identified by at least one sending public-mode device using a SCF in its SST client;

Passively receive at least one communication from a set comprised of at least one of the following—private search inquiry, alert, message or other communication—based on at least one SFA of the recipient device identified by at least one sending affinity public-mode device using a SCF in its SST client; and Be in private mode, wherein the ID of the said private mode device is not detectable by other network devices.

* * * * *